United States Patent [19]
Allen

[11] Patent Number: 6,086,551
[45] Date of Patent: *Jul. 11, 2000

[54] FLEXIBLE COMPRESSION AND STABILIZING ORTHOTICS

[76] Inventor: Cheryl L. Allen, 13505 Cedar Ct. East, Sumner, Wash. 98390

[*] Notice: This patent is subject to a terminal disclaimer.

[21] Appl. No.: 09/347,934

[22] Filed: Jul. 6, 1999

Related U.S. Application Data

[60] Continuation of application No. 09/071,646, May 1, 1998, which is a division of application No. 08/652,644, May 31, 1996, Pat. No. 5,782,790.

[51] Int. Cl.⁷ .............................. A61F 5/00; A61F 15/00; A41B 0/00; A41D 1/04
[52] U.S. Cl. .................. 602/19; 602/5; 602/75; 2/102; 2/69
[58] Field of Search ..................... 602/5, 19, 20, 602/23, 26, 75; 2/69, 109, 243.1, 255, 409

[56] References Cited

U.S. PATENT DOCUMENTS

| | | |
|---|---|---|
| 3,983,870 | 10/1976 | Herbert et al. . |
| 4,027,667 | 6/1977 | Swallow et al. . |
| 4,400,832 | 8/1983 | Kinder . |
| 4,709,694 | 12/1987 | O'Connell . |
| 4,781,178 | 11/1988 | Gordon . |
| 5,031,609 | 7/1991 | Fye . |
| 5,109,546 | 5/1992 | Dicker . |
| 5,146,932 | 9/1992 | McCabe . |
| 5,154,690 | 10/1992 | Shiono . |
| 5,188,585 | 2/1993 | Peters . |
| 5,210,877 | 5/1993 | Newman . |
| 5,221,252 | 6/1993 | Caprio, Jr. et al. . |
| 5,356,371 | 10/1994 | Hubbard . |
| 5,367,708 | 11/1994 | Fujimoto . |
| 5,370,606 | 12/1994 | Martel et al. . |
| 5,412,957 | 5/1995 | Bradberry et al. . |
| 5,413,553 | 5/1995 | Downes . |
| 5,425,702 | 6/1995 | Carn et al. . |
| 5,449,341 | 9/1995 | Harris . |
| 5,498,234 | 3/1996 | Martel et al. . |
| 5,582,583 | 12/1996 | Ballantyne . |
| 5,694,645 | 12/1997 | Triplette . |
| 5,708,978 | 1/1998 | Johnsrud . |
| 5,754,982 | 5/1998 | Gainer . |
| 5,782,790 | 7/1998 | Allen ......................................... 602/75 |
| 5,957,873 | 9/1999 | Allen ......................................... 602/19 |

OTHER PUBLICATIONS

Blair, E., et al., "A Study of a Dynamic Proximal Stability Splint in the Management of Children with Cerebral Palsy," *Developmental Medicine and Child Neurology*, vol. 37, 1995, pp. 544–554.

*Primary Examiner*—Richard J. Apley
*Assistant Examiner*—Kim M. Lee
*Attorney, Agent, or Firm*—Christensen O'Connor Johnson & Kindnesspllc

[57] ABSTRACT

A flexible compression and stabilizing orthotic for providing sensory input and body awareness to a person suffering from a neurological disorder, autism, proprioceptive and sensory deficits, or hypersensitivity is disclosed. The orthotic is made from a multidirectional stretchable spandex material.

18 Claims, 2 Drawing Sheets

FLEXIBLE COMPRESSION AND STABILIZING ORTHOTICS

CROSS-REFERENCE TO RELATED APPLICATIONS

This application is a continuation of U.S. patent application Ser. No. 09/071,646 filed May 1, 1998, which is a divisional application of U.S. patent application Ser. No. 08/652,644, filed May 31, 1996, now U.S. Pat. No. 5,782,790, the benefit of the priority of the filing dates of which is hereby claimed under 35 U.S.C. § 120.

FIELD OF THE INVENTION

The present invention relates in general to an orthotic device, and in particular to a flexible compression and stabilizing orthotic that provides sensory input and is useful in improving the motor control of an individual suffering from a neurological disorder.

BACKGROUND OF THE INVENTION

Individuals suffering from many neurological disorders are typically afflicted with impaired motor control. Individuals suffering from neurological disorders often also suffer from proprioception and pressure-sensory deficits, which prevent the reception of stimulation and result in a lack of sensory input from their environment. The lack of sensory input tends to render the afflicted individual unaware of his or her environment. Ultimately, this lack of sensory input results in the lack of muscular and motor control. In many instances, neurological disorders are outwardly manifested by muscular incoordination, body tremors, varying degrees of paralysis, an inability to coordinate voluntary muscular movement, and speech disturbances, among other disabilities.

Traditional treatments for those suffering from neurological disorders include physical and occupational therapy, orthopedic bracing and surgery, and speech training. In addition to physical exercises designed to strengthen muscles and improve motor control, physical therapies also include massage and deep-pressure therapy. Beyond providing beneficial stimulation, massage appears to increase sensory perception and, in some instances, improve muscular and motor control. Massage is believed to improve muscular and motor control through pressure input where sensory feedback is provided to the afflicted individual. However, the benefits of massage are only short lasting and provide only temporary improvements.

In addition to physical therapies, compression and support orthotics have also been used in attempts to improve muscular and motor control in individuals suffering from certain neurological disorders. In general, these support orthotics stabilize a part of the body through structural support. Examples of support orthotics include orthopedic braces and postural equipment having external supports, and compression supports such as braces and wraps typically made from relatively heavy, elastic, stretchable materials. Dynamic orthotics, including dynamic splints, are a type of orthotic that provide support, control, and sensory feedback, and at the same time, allow and guide the wearer's movements. Body splints, which may be applied to various parts of the body including the torso, arms, legs, hands, feet, and head, provide stabilization to the body part primarily through structural support. In fact, dynamic splinting has reportedly been useful in controlling abnormal tone, stabilizing posture, and improving the functional abilities of individuals suffering from neurological disorders (Blair et al., A Study of Dynamic Proximal Stability Splint in the Management of Children with Cerebral Palsy," *Developmental Medicine and Child Neurology*, Vol. 37, pp. 544–554, 1995).

In general, a dynamic splint is a close fitting orthotic made from an elastic, stretchable material that applies a dynamic correctional force to a particular body part of the wearer. Typically, splints are made from materials including thermoplastics, plasters, neoprene, and the like. While each of these materials provides support, splints made from these materials are disadvantageous as they tend to be bulky, retain moisture emitted from the skin of the wearer, and often result in overheating during use. Although improvements in these orthotics have been made to provide a decrease in the amount of moisture retention and heating caused by the wearing of these devices, these orthotics are often uncomfortable to the wearer. Moreover, these orthotics address structural stabilization of a body part at the expense of orthotic flexibility.

Accordingly, there remains a need in the art for a flexible compression and stabilizing orthotic that provides compression to a body part of a wearer and, at the same time, is breathable, comfortable and does not inhibit movement of the wearer. In addition, there is a need for a method for providing sensory input and improving the muscular and motor control of a person suffering from a neurological disorder that overcomes the disadvantages associated with the traditional orthotic devices noted above. The present invention seeks to fulfill these needs and provides further related advantages.

SUMMARY OF THE INVENTION

The present invention provides a method for providing sensory input and body awareness to a person suffering from a neurological disorder characterized by impaired motor control, autism, proprioceptive deficits, deep-sensory deficits, or hypersensitivity. In the method, a flexible compression and stabilizing orthotic made from a multidirectional stretchable spandex material is applied to the afflicted person. The flexible compression orthotic allows for freedom of movement and provides sensory input through a compression load to the portion of the body covered by the orthotic. The flexible compression orthotic may be a wearable article such as a shirt, pants, unitard, glove, stocking, hood, torso wrap, compression sleeve, or compression band. The orthotic may also be a swaddle.

In a preferred embodiment, the spandex material is a 20:80 blend of Lycra® and nylon. The compression load of the orthotic is provided by its close fitting to a body part of the wearer. In a preferred embodiment, the size of the orthotic is about 70 to about 85% of the size of the body part to be covered by the orthotic. In the method for providing sensory input to a person suffering from a neurological disorder characterized by impaired motor control, use of the flexible compression orthotic results in an improvement in motor control including improvements in grading, stability, balance, movement, calming, vocalization, and feeding.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
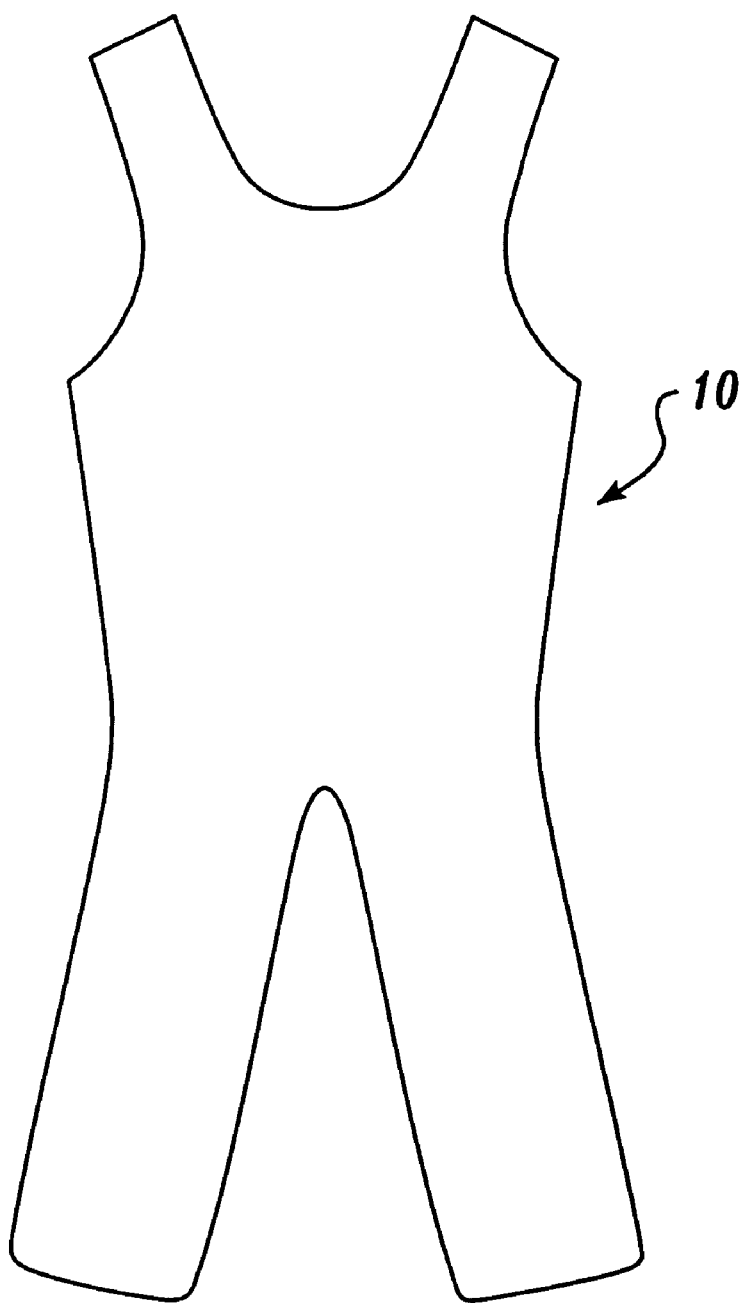
FIG. 1 is an illustration of a flexible compression unitard, a representative flexible compression and stabilizing orthotic of the present invention.

The present invention generally provides a flexible compression and stabilizing orthotic that is useful in providing sensory input and body awareness to the orthotic wearer. More particularly, the flexible compression orthotic is useful in improving the motor control of a person suffering from a neurological disorder. Methods for providing increased sensory input and body awareness and improving the motor control of a person suffering from a neurological disorder involving wearing the flexible compression and stabilizing orthotic are also provided. The orthotic useful in the present invention is made from a multidirectional stretchable material that allows freedom of movement and provides sensory input through a compression load to the portion of the body part covered by the orthotic.

In addition to providing a degree of structural support to the portion of the body covered by the orthotic, the orthotic useful in this invention provides sensory input and body awareness to the wearer. The sensory input is believed to provide the wearer with an awareness of his or her environment. The sensory input and resulting awareness of the environment are believed to be responsible for the improvements in muscular and motor capabilities of a wearer who suffers from a neurological disorder characterized by impaired motor control. The sensory input from the flexible compression orthotic also provides for improvements in body control and behavior for persons, particularly children, suffering from a variety of conditions and disorders including hypersensitivity, proprioceptive and deep sensory deficits, and autism.

The orthotic of this invention is a dynamic orthotic in that it allows and guides free movement while, at the same time, providing stabilizing support and control. The dynamic aspect of the orthotic arises from its flexibility, which is imparted to the orthotic by the multidirectional stretchable material from which the orthotic is made. The sensory input provided to the wearer by the orthotic is a result of the compression load applied to the portion of the body covered by the orthotic. The substantially uniform compression load is due primarily to the nature of the multidirectional stretchable material.

Generally, the flexible compression orthotic is individually prescribed and designed to address the specific neurological and functional requirements of the wearer. In general, the flexible orthotic is a wearable article and is close fitting, preferably worn next to the skin. While the flexible orthotic of the present invention may take any one of a number of forms of wearable articles, the orthotic may be a long- or short-sleeved shirt, long or short pants, a unitard, a glove, a stocking, a hood, a torso wrap, a compression sleeve, or a compression band. The flexible orthotic may also be configured as a swaddle for use with small children.

As noted above, the sensory input provided by the orthotic of this invention results from the compression load applied to the portion of the body covered by the orthotic. The compression load is provided primarily by close fitting of the orthotic to the particular portion of the body covered by the orthotic. In the context of the present invention, close fitting of the orthotic depends on the relative sizes of the orthotic and the portion of the body over which the orthotic is worn. In a preferred embodiment, the size of the orthotic is from about 65 to about 85 percent of the size of the portion of the body over which the orthotic is worn. In a particularly preferred embodiment, the size of the orthotic is about 70 to about 85 percent of the size of the portion of the body over which the orthotic is worn. As used herein, the term "size" refers to the circumference of the orthotic or the portion of the body over which the orthotic is worn. For example, if the wearer has a torsal circumference of 26 inches, the orthotic would preferably be made with a circumference of about 20 inches.

Unlike other stabilizing orthotics, the flexible compression orthotic of the present invention does not include external bracing or supports. Rather, the flexible orthotic of this invention provides for complete freedom of movement. Accordingly, while traditional support orthotics are directed to enhancing stability of movement and motor control by providing structural support, the flexible compression of the orthotic of this invention provides sensory input to muscle groups to improve the functional capacity of these muscles and, ultimately, to educate the impaired muscles toward more normal function. The orthotic of the present invention is designed to simulate a massage to the muscles covered by the orthotic. In this context, the orthotic may be thought of as an exerciser where tone and control are developed in muscles over which the orthotic is worn.

The flexible compression orthotic of this invention may be configured to be worn over any portion of the body, including the head, arms, legs, torso, hands, and feet. For example, the orthotic may be worn over the torso and both arms in which case the orthotic is configured in the form of a shirt (i.e., a flexible compression shirt). As noted above, the orthotic may also be worn over both legs as a pair of pants. The orthotic may also take the form of a suit such as a unitard worn over the torso and arms and legs (i.e., a flexible compression unitard), a stocking worn over a foot, a glove worn over a hand, or a hood worn over the head. The orthotic may also be worn as a sleeve, legging, or band, to be worn over a portion of an arm, a leg, or the torso, respectively.

Figure 2A:
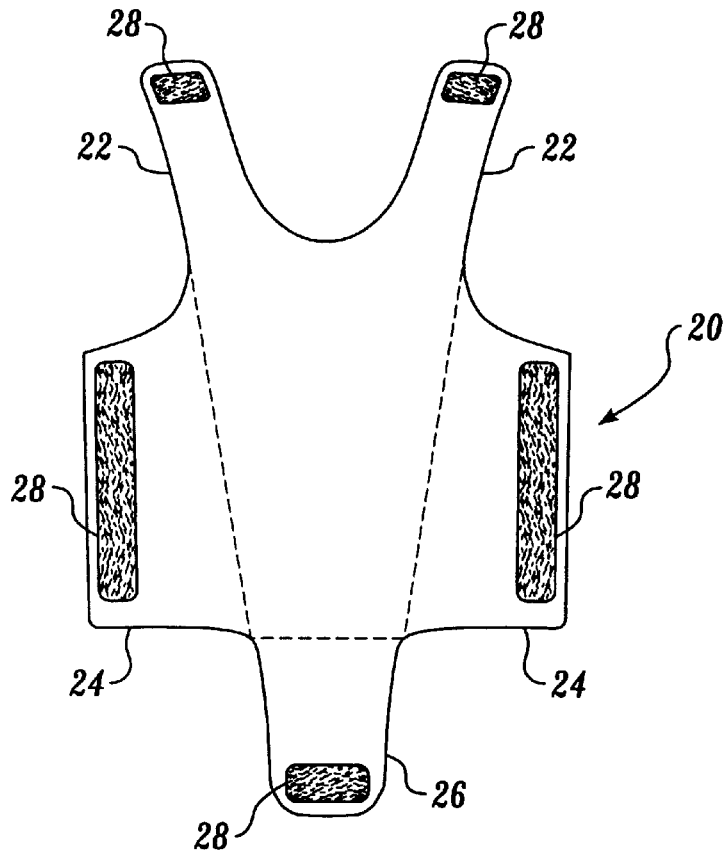
FIG. 2A is an illustration of the front portion of a flexible compression vest (torso wrap), a representative flexible compression orthotic of the present invention.

A variety of embodiments of flexible compression orthotics useful in the present invention are envisioned. For example, representative flexible compression orthotics including a flexible compression unitard and flexible compression vest (torso wrap) are illustrated in FIGS. 1 and 2A and B, respectively. Referring to FIG. 1, flexible compression unitard 10 is a one-piece suit having a sleeveless upper portion and a lower portion having legs. The unitard applies compression to the body throughout the torso, through the shoulders, and to the legs. The lengths of the legs of the unitard are variable and may be ankle length, calf length or knee length.

The flexible compression orthotics useful in this invention may be worn in combination. For example, the unitard may be worn in combination with a shirt. In such a combination, the wearer's torso is covered with a double layer of the multidirectional stretchable material resulting from the overlap of the materials of the shirt and unitard. The double layer provides increased stability as well as increased sensory input, and may be advantageous to certain wearers having more extreme stability and sensory input needs. While flexible compression orthotics useful in this invention include orthotics made from a single layer of a multidirectional stretchable material, in some instances, flexible compression orthotics made from a double layer of a multidirectional stretchable material are preferable. For example, the flexible compression band, sleeve, and torso wrap (flexible compression vest) are preferably double-layered orthotics.

Figure 2B:
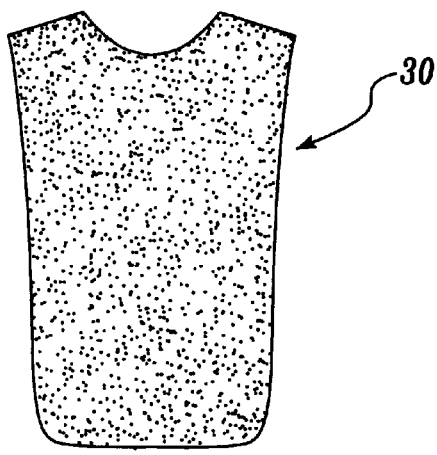
FIG. 2B is an illustration of the back portion of the flexible compression vest.

Referring to FIGS. 2A and 2B, the flexible compression vest comprises a front portion 20 made from a double layer of a multidirectional stretchable material and having shoulder straps 22, side flaps 24, and lower strap 26. Each of straps 22 and 26 and flaps 24 has a Velcro® fastening strip for attaching the front portion of the vest to the back portion of the vest, thus securing the vest on the wearer. Referring to FIG. 2B, the back portion 30 serves primarily to secure the front portion on the wearer. The back portion 30 may be made from a variety of materials including, for example, a stretchable material having a complementary Velcro® fastening means or other suitable material that provides for the secure attachment of the front portion of the vest to the back portion. In a preferred embodiment, back portion 30 is a terry back nylon neoprene where the terry portion of the neoprene back serves to secure the Velcro® fastening strips 28 of the front portion of the vest to the back portion. The flexible compression vest illustrated in FIGS. 2A and 2B has the advantage of being adjustable to the size of the wearer, and therefore may be useful in situations where a single vest may be shared by a number of different size wearers.

In contrast to some other orthotic devices, the flexible compression orthotics useful in this invention do not require a break-in period, and consequently their effective use may commence from initial wearings.

The advantageous properties of the flexible compression orthotic are primarily imparted by the multidirectional stretchable material from which the orthotic is made. In a preferred embodiment, the multidirectional stretchable material is a spandex material. As used herein, the term "spandex" refers to polyurethane containing fiber. In a preferred embodiment, the spandex material is a Lycra®-based material (trademark of the Dupont Company). Preferred Lycra®-based materials include blends of Lycra® and nylon. In a preferred embodiment, the spandex material is a 20:80 blend of Lycra® and nylon having a weight of 8.5 ounces per yard. Unlike many orthotics that possess differential stretch properties, the spandex material useful in the orthotic of this invention is a multidirectional stretchable material. By way of illustration, many spandex materials are bidirectional and have directions of maximum and minimum stretch. Typically, these materials have a minimum stretch direction where the material may be elongated from about 150 to about 350 percent of its resting length, and a maximum stretch direction where the material may be elongated from about 200 to about 500 percent of its resting length. In contrast, the multidirectional stretchable material useful in this invention is stretchable in all directions, does not have maximum and minimum stretch directions, and as a result provides a substantially uniform compression load when properly sized and applied to a portion of a body.

In addition to providing flexibility and substantially uniform compression when configured into a properly sized orthotic, the spandex material allows freedom of movement and provides for intimate skin contact and sensory input through compression to the muscles covered by the orthotic (i.e., massage simulation). The spandex material is also breathable and allows for the evaporation of moisture from the skin of the orthotic wearer. Orthotics made from this spandex material also avoid overheating. Furthermore, unlike bulkier materials, such as neoprene and heavier weight Lycra®-based materials, the spandex material useful in this invention remains in place on the wearer's body and does not "bunch up" during the course of its wear. Also, because of the multidirectional properties of the spandex material, the orthotic of this invention does not require elastic bands or other such means to hold the orthotic in place on a wearer. More importantly, unlike the spandex material useful in this invention, the bulk of the heavier weight elastic materials noted above prevents intimate contact with the wearer's skin and provides much less connection between the compression and the muscles over which the orthotic is worn. Consequently, orthotics made from such bulky materials are much less effective in providing sensory input to the wearer. As indicated by their primary uses in orthotic bracing, the bulkier elastic materials are effective as stabilizing structural supports.

The present invention provides a method for improving the motor control of a person suffering from a neurological disorder characterized by impaired motor control. In the method, the wearing of a flexible compression and stabilizing orthotic made from a multidirectional stretchable spandex material as described above by a person suffering from such a neurological disorder, results in an improvement in motor control of the orthotic wearer. While wearing the flexible compression orthotic described above may improve the muscular and motor control of a person suffering from a variety of neurological disorders, wearing of the orthotic has resulted in improvement in motor control of individuals suffering from neurological disorders such as, for example, encephalopathy including diffuse static encephalopathy and cerebral palsy syndromes. As used herein, the term "cerebral palsy syndrome" refers to a disability resulting from damage to the brain, typically occurring before or during birth and outwardly manifested by muscular incoordination. Generally, cerebral palsy is a paralysis, a complete or partial loss of function or sensation in a part of the body, characterized by involuntary tremors. Cerebral palsy syndromes refer to a number of motor disorders involving impaired involuntary movement. The syndromes fall within four main categories: (1) spastic syndromes (i.e., paralysis including hemiplegia, paraplegia, diplegia, and quadriplegia), (2) athetoid or dyskinetic syndromes (i.e., nervous disorder marked by continual slow movements usually of the extremities), (3) ataxic syndromes (i.e., an inability to coordinate voluntary muscular movements), and (4) mixed forms of these syndromes (e.g., spasticity and athetosis, ataxia and athetosis). The improvements in motor control observed for orthotic wearers suffering from neurological disorders such as those noted above include improvements in grading, stability, balance, movement, calming, vocalization, and feeding, among others.

The use of the flexible compression orthotic of this invention has also resulted in improvements in motor control, balance, and stability in children diagnosed with a variety of neuromuscular disorders and conditions including early motor difficulties, hypertonus, proprioceptive deficit, deep-pressure sensory deficit, hypersensitivity, and other motor coordination difficulties. For example, improvements in movements and tone control upon wearing the flexible compression orthotic configured as short pants were observed for an eight-month-old boy diagnosed with early motor difficulties with hypertonus and proprioceptive and deep-pressure sensory deficits. The flexible compression orthotic decreased the hypertonus and improved the control of movement of his arms and legs. A three-month-old boy diagnosed with significant sensory difficulties, including hypersensitivity, increased extensor posturing, primary difficulties with stability and movement control, and showing strong tremors and large tone fluctuations, showed improvements in organized motion when wrapped in a flexible compression orthotic configured as a swaddle. Swaddling with the flexible compression orthotic produced a calming effect for the child and allowed the child to sleep more readily. This child also wore a flexible compression unitard and shirt during the day and showed improved balance, stability, and movement control during periods of usage. While the motor skills of the child gained during usage were initially lost during periods of nonuse, over time the motor skills gained during periods of orthotic usage carried over into periods when the child was not wearing the orthotic. Such a learning curve for improvements from the use of the flexible compression orthotic is not uncommon.

In other cases, a therapist who had been working for six months with a two-year-old boy who was unable to sit up on his own, unable to hold his head erect, and made no sounds or vocalized at all, observed almost immediate improvements in posture and muscular control as well as initiation of vocalization upon his wearing of the flexible compression unitard. For an ambulatory five-year-old girl with mixed spastic/athetoid quadriplegia, wearing flexible compression pants resulted in decreased equinus and improvements in balance in standing and walking. A six-year-old boy with severe visual difficulties and mild athetoid-type motor incoordination was able to maintain successive jumping, showed smooth running, and became more coordinated in appearance and standing upon wearing the flexible compression unitard. A fifteen-month-old child having high-tone athetosis was immediately observed to have quieted tone and movement on wearing the flexible compression unitard. A two-year-old boy suffering from extreme hypersensitivity and disorganized with an ataxic motor involvement was able to interact with his environment when wearing the flexible compression unitard. In this case, the flexible compression unitard was worn throughout the day and new skills gained during the periods of usage were gradually generalized to times when the orthotic was not worn. In addition to flexible compression orthotics configured as shirts, pants, and unitards, the use of flexible compression gloves has also been shown to be effective in providing sensory input and improving motor control and hand use.

Improvements in motor control of persons suffering from impaired motor control have been observed soon after the flexible compression orthotic is applied to the afflicted person. In general, improvements occur during periods of orthotic use, increase over time, and depend on the extent that the orthotic is worn. Although the orthotic may be continuously worn, learned improvements in motor control have been observed for periods after the orthotic is removed. It appears that the length of time of improved motor control during periods of nonuse increases with the frequency and duration of use of the orthotic.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A flexible compression and stabilizing-orthotic for providing sensory input and body awareness to a person suffering from a neurological disorder characterized by impaired motor control, or autism, or proprioceptive deficits, or deep-sensory deficits, or hypersensitivity, wherein the orthotic consists essentially of a multidirectional stretchable spandex material that does not provide lines of pull in predetermined direction to a wearer's body but rather allows for freedom of movement and provides sensory input through a compression load to the portion of the body covered by the orthotic, wherein the compression load is provided by close fitting of the orthotic to a wearer's body part, and wherein the orthotic is from about 65 to about 85 percent of the size of the body part.

2. The orthotic of claim 1 wherein the size of the orthotic is about 70 to about 85 percent of the size of the body part.

3. The orthotic of claim 1 wherein the neurological disorder is an encephalopathy.

4. The orthotic of claim 3 wherein the encephalopathy is diffuse static encephalopathy.

5. The orthotic of claim 1 wherein the neurological disorder is a cerebral palsy syndrome.

6. The orthotic of claim 5 wherein the cerebral palsy syndrome is selected from a spastic syndrome, an athetoid syndrome, a dyskinetic syndrome, an ataxic syndrome, and mixed forms thereof.

7. The orthotic of claim 6 wherein the spastic syndrome is a paralysis selected from hemiplegia, paraplegia, diplegia, and quadriplegia.

8. The orthotic of claim 1 wherein the orthotic is a wearable article selected from a shirt, pants, a unitard, a glove, a stocking, a hood, a torso wrap, a compression sleeve, a compression band.

9. The orthotic of claim 1 wherein the orthotic is a swaddle.

10. The orthotic of claim 1 wherein the spandex material is a Lycra®-based material.

11. The orthotic of claim 1 wherein the spandex material is a blend of Lycra® and nylon.

12. The orthotic of claim 1 wherein the spandex material is a 20:80 blend of Lycra® and nylon.

13. The orthotic of claim 1 wherein the portion of the body covered by the orthotic is selected from the head, an arm, a leg, the torso, a hand, and a foot.

14. The orthotic of claim 1 wherein the sensory input results in an improvement in motor control.

15. The orthotic of claim 14 wherein the improvement is selected from improvements in grading, stability, balance, movement, calming, vocalization, and feeding.

16. The orthotic of claim 1 wherein the orthotic is made from a single layer of a multidirectional stretchable material.

17. The orthotic of claim 1 wherein the orthotic is made from a double layer of a multidirectional stretchable material.

18. The orthotic of claim 1 wherein the orthotic is made from multiple layers of a multidirectional stretchable material.

* * * * *

UNITED STATES PATENT AND TRADEMARK OFFICE
CERTIFICATE OF CORRECTION

PATENT NO. : 6,086,551
DATED : July 11, 2000
INVENTOR(S) : C.L. Allen

It is certified that error appears in the above-identified patent and that said Letters Patent is hereby corrected as shown below:

| COLUMN | LINE | |
|---|---|---|
| 8 (Claim 1, | 1 line 1) | "stabilizing-orthotic" should read --stabilizing orthotic-- |
| 8 (Claim 1, | 8 line 8) | "direction" should read --directions-- |

Signed and Sealed this

Twenty-second Day of May, 2001

Attest:

NICHOLAS P. GODICI

*Attesting Officer*  Acting Director of the United States Patent and Trademark Office